Jan. 31, 1956 E. G. FISHER Plant Pat. 1,453
ROSE PLANT
Filed March 1, 1955
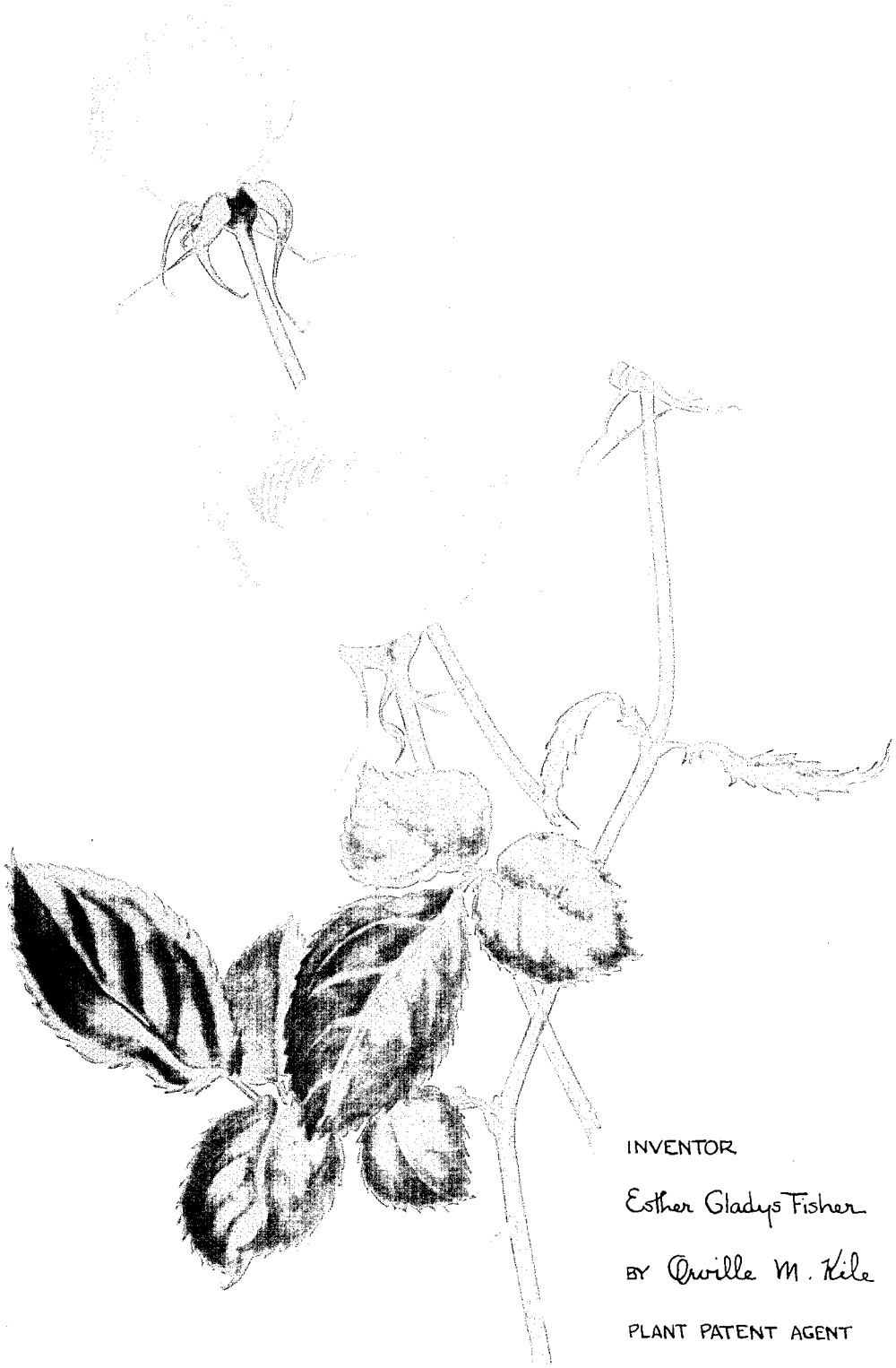
INVENTOR
Esther Gladys Fisher
BY Orville M. Kile
PLANT PATENT AGENT United States Patent Office Plant Pat. 1,453

Patented Jan. 31, 1956

1,453

ROSE PLANT

Esther Gladys Fisher, Woburn, Mass., assignor to Arnold-Fisher Company, Woburn, Mass.

Application March 1, 1955, Serial No. 491,552

1 Claim. (Cl. 47—61)

My present invention relates to an improvement in rose plants and is new and distinct from any other variety known to me. Although the female parent is a hybrid polyantha and the male parent contains some hybrid tea "blood," it is of the type known commercially as a floribunda rose variety.

The female parent was Floradora (unpatented), and the male parent was Fashion (Plant Patent No. 789)—the cross having been made by me at the Woburn, Massachusetts, greenhouses of which I am part owner.

Asexual reproduction by means of buds and grafts has been accomplished by me at the same location, and the characteristics of the new variety appear to be permanent.

Outstanding features of my new variety are its adaptability to greenhouse culture, and the brilliant color of its flower, popularly known as coral or flamingo, which falls between the colors of the flowers of its parents. Its color, long stems, and bright foliage make it most acceptable for use in corsages and for home decoration.

Illustrations accompanying these specifications show three specimens of the flower of my new variety in various stages of opening, together with portions of the stems and foliage.

In the following detailed description, color plate numbers refer to Ridgway's Color Standards and Nomenclature. Where no plate number is used, the ordinary dictionary meaning of the nomenclature is intended.

THE PLANT

Form: Vigorous bush.

Growth habit: Vigorous grower, attaining a height of 7 to 8 feet under usual greenhouse culture.

Blooming habit: Very prolific producer of flowers when grown as a greenhouse rose.

Stems: Long; slender but strong. Internodes short and slightly staggered. Color approximately Oil Green (Plate V), usually slightly bronzed.

Thorns: Rather numerous; sharp; slender; outward pointing; usually reddish-tinged.

Foliage:

*Quantity.*—Plentiful.

*Type.*—Pinnately compound, usually with 3 to 5 leaflets, the three of first set often being joined so as to form a single lobed leaf.

*Color.*—Beautiful bright green on upper surface, approximately Forest Green (Plate XVII). Under surface is approximately Light Elm Green (Plate XVII).

*Texture.*—Leathery but not heavy.

*Size.*—Terminal leaflets 2½ to 3 inches long by 1¾ to 2 inches wide. Pairs of lateral leaves progressively smaller.

*Rachis.*—Slender; grooved above; smooth on under side except for an occasional small thorn. Usually somewhat bronzed.

*Stipules.*—Narrow; short; clinging except for small points.

*Shape.*—Broad oval with acuminate tip. Edge finely serrated.

BLOOM

Bud:

*Color.*—Nearest found in Ridgway's is between Geranium Pink and Rose Doree (Plate I), but with a slight salmon tinge.

*Size.*—1¼ inches long, just before unfurling.

*Shape.*—Conical at first, becoming winged as it opens.

*Opening.*—Opens slowly.

*Peduncle.*—Short; slender but very strong; smooth; approximately Oil Green (Plate V).

*Sepals.*—Mostly simple, sometimes with one sepal slightly foliaceous. Reflex early, clasping stem.

Flower:

*Borne.*—In small clusters. Can be controlled in the greenhouse to produce a single rose on a long stem, by disbudding the side shoots near top of stem.

*Form.*—High-centered like a hybrid tea, later opening cup-shaped.

*Color.*—The inside surface of the petal more orange tone in its color than the outside surface, and lies between Rose Doree (Plate I) and Peach Red (Plate I).

*Size.*—Medium. When fully expanded, the flower averages 3 to 3½ inches in diameter.

*Petalage.*—Double, with 25 to 35 petals.

*Longevity.*—Lasts well as cut flower.

*Fragrance.*—Slight.

Petals:

*Substance.*—Medium.

*Aspect.*—Slightly velvety on inner surface. Outer surface silky.

*Form.*—Approximately round, with single sharp point at tip.

COMPARISON

My new variety resembles each of its parents in some features and in many respects falls between the two, principally as follows:

*Flower*

*Form.*—The open flower of Fashion is very flat, showing all the stamens and giving the appearance of a single rose. The flower of Floradora is very double, giving the impression of a full, fluffy rose. The flower of my new variety ranges between the two in form.

*Color.*—Fashion is a light salmon color and Floradora is a deep orange-rose or nasturtium color. My new variety is flamingo to coral, in popular terms—deeper than Fashion and lighter than Floradora (although the latter turns much lighter and faded when old). The lighter shade of my new rose is more acceptable for greenhouse work.

Foliage and growth of my new variety are much the same as those of Floradora, but Fashion has dull foliage and does not do well as a greenhouse rose.

Having thus disclosed my invention, I claim:

The new and distinct variety of floribunda rose plant, substantially as herein shown and described, characterized particularly by the combination of its strong growth; its adaptability to greenhouse culture; its attractive bright green foliage; its long stems; and the Rose Doree to Peach Red color of its buds and individual flowers of miniature hybrid-tea form.

No references cited.